United States Patent
Rajasekharan et al.

(10) Patent No.: US 10,801,990 B2
(45) Date of Patent: Oct. 13, 2020

(54) ALKALINITY MEASUREMENT OF AN AQUEOUS SAMPLE

(71) Applicant: Hach Company, Loveland, CO (US)

(72) Inventors: Vishnu Vardhanan Rajasekharan, Fort Collins, CO (US); Corey Alan Salzer, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 157 days.

(21) Appl. No.: 15/955,124

(22) Filed: Apr. 17, 2018

(65) Prior Publication Data

US 2019/0317044 A1 Oct. 17, 2019

(51) Int. Cl.
  *G01N 27/416* (2006.01)
  *G01N 27/30* (2006.01)

(52) U.S. Cl.
  CPC ....... *G01N 27/4165* (2013.01); *G01N 27/302* (2013.01); *G01N 27/308* (2013.01); *G01N 27/4167* (2013.01)

(58) Field of Classification Search
  CPC . G01N 27/4165; G01N 27/4146; G01N 33/18
  See application file for complete search history.

(56) References Cited

U.S. PATENT DOCUMENTS

2012/0132544 A1* 5/2012 Lawrence ............ G01N 27/302 205/782
2017/0010238 A1* 1/2017 Johnson ............. G01N 27/4167

FOREIGN PATENT DOCUMENTS

GB 2518263 * 3/2015 .......... G01N 27/302

OTHER PUBLICATIONS

Cheng, L., Charles W. et al., "Automatic online buffer capacity (alkalinity) measurement of wastewater using an electrochemical cell", Environmental Technology, 37 (19), 2016, 15 pages, Taylor and Francis Ltd., United Kingdom.

* cited by examiner

*Primary Examiner* — Luan V Van
*Assistant Examiner* — Caitlyn Mingyun Sun
(74) *Attorney, Agent, or Firm* — Ference & Associates LLC

(57) ABSTRACT

An embodiment provides a method for compensating for inteferants in measurement of alkalinity in a reagent-less system, including: introducing an aqueous sample into a measurement device comprising one or more series of electrodes; applying an electrical signal to the aqueous sample using the one or more series of electrodes, wherein the electrical signal is selected from the group consisting of: current and voltage; identifying, during application of the electrical signal, that the electrical signal reaches an oxidation threshold and measuring, prior to reaching the oxidation threshold, a first electrical response to the electrical signal, the first electrical response attributable to interferants in the aqueous sample; identifying, during application of the electrical signal, that the electrical signal reaches an endpoint and measuring, from the oxidation threshold to the endpoint, a second electrical response to the electrical signal; and measuring an alkalinity of the aqueous sample based upon a difference between the first electrical response and the second electrical response. Other aspects are described and claimed.

10 Claims, 6 Drawing Sheets

ALKALINITY MEASUREMENT OF AN AQUEOUS SAMPLE

FIELD

This application relates generally to water quality measurement, and, more particularly, to mitigation of interferences in reagent-less measurement of alkalinity in an aqueous sample.

BACKGROUND

Ensuring water quality is critical in a number of industries such as pharmaceuticals and other manufacturing fields. Additionally, ensuring water quality is critical to the health and well-being of humans, animals, and plants which are reliant on the water for survival. One parameter of the water that may be measured is the alkalinity. Measurement of alkalinity may allow for identification or computation of other parameters of the water, for example, buffering capacity of the water, which allows for identifying the overall quality of the water. One method to test for alkalinity includes a complex titration process, requires chemicals to be added to the sample, and also requires maintenance of the sampling system.

BRIEF SUMMARY

In summary, one embodiment provides a method for compensating for interferants in measurement of alkalinity in a reagent-less system, comprising: introducing an aqueous sample into a measurement device comprising one or more series of electrodes; applying an electrical signal to the aqueous sample using the one or more series of electrodes, wherein the electrical signal is selected from the group consisting of: current and voltage; identifying, during application of the electrical signal, that the electrical signal reaches an oxidation threshold and measuring, prior to reaching the oxidation threshold, a first electrical response to the electrical signal, the first electrical response attributable to interferants in the aqueous sample; identifying, during application of the electrical signal, that the electrical signal reaches an endpoint and measuring, from the oxidation threshold to the endpoint, a second electrical response to the electrical signal; and measuring an alkalinity of the aqueous sample based upon a difference between the first electrical response and the second electrical response.

Another embodiment provides a measurement device for compensating for interferants in measurement of alkalinity in a reagent-less system, comprising: at least one chamber; one or more series of electrodes at least partially disposed within one of the at least one chamber; a processor; and a memory device that stores instructions executable by the processor to: introduce an aqueous sample into a measurement device comprising one or more series of electrodes; apply an electrical signal to the aqueous sample using the one or more series of electrodes, wherein the electrical signal is selected from the group consisting of: current and voltage; identify, during application of the electrical signal, that the electrical signal reaches an oxidation threshold and measuring, prior to reaching the oxidation threshold, a first electrical response to the electrical signal, the first electrical response attributable to interferants in the aqueous sample; identify, during application of the electrical signal, that the electrical signal reaches an endpoint and measuring, from the oxidation threshold to the endpoint, a second electrical response to the electrical signal; and measure an alkalinity of the aqueous sample based upon a difference between the first electrical response and the second electrical response.

A further embodiment provides a product for compensating for interferants in measurement of alkalinity in a reagent-less system, comprising: a storage device having code stored therewith, the code being executable by the processor and comprising: code that introduces an aqueous sample into a measurement device comprising one or more series of electrodes; code that applies an electrical signal to the aqueous sample using the one or more series of electrodes, wherein the electrical signal is selected from the group consisting of: current and voltage; code that identifies, during application of the electrical signal, that the electrical signal reaches an oxidation threshold and measuring, prior to reaching the oxidation threshold, a first electrical response to the electrical signal, the first electrical response attributable to interferants in the aqueous sample; code that identifies, during application of the electrical signal, that the electrical signal reaches an endpoint and measuring, from the oxidation threshold to the endpoint, a second electrical response to the electrical signal; and code that measures an alkalinity of the aqueous sample based upon a difference between the first electrical response and the second electrical response.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
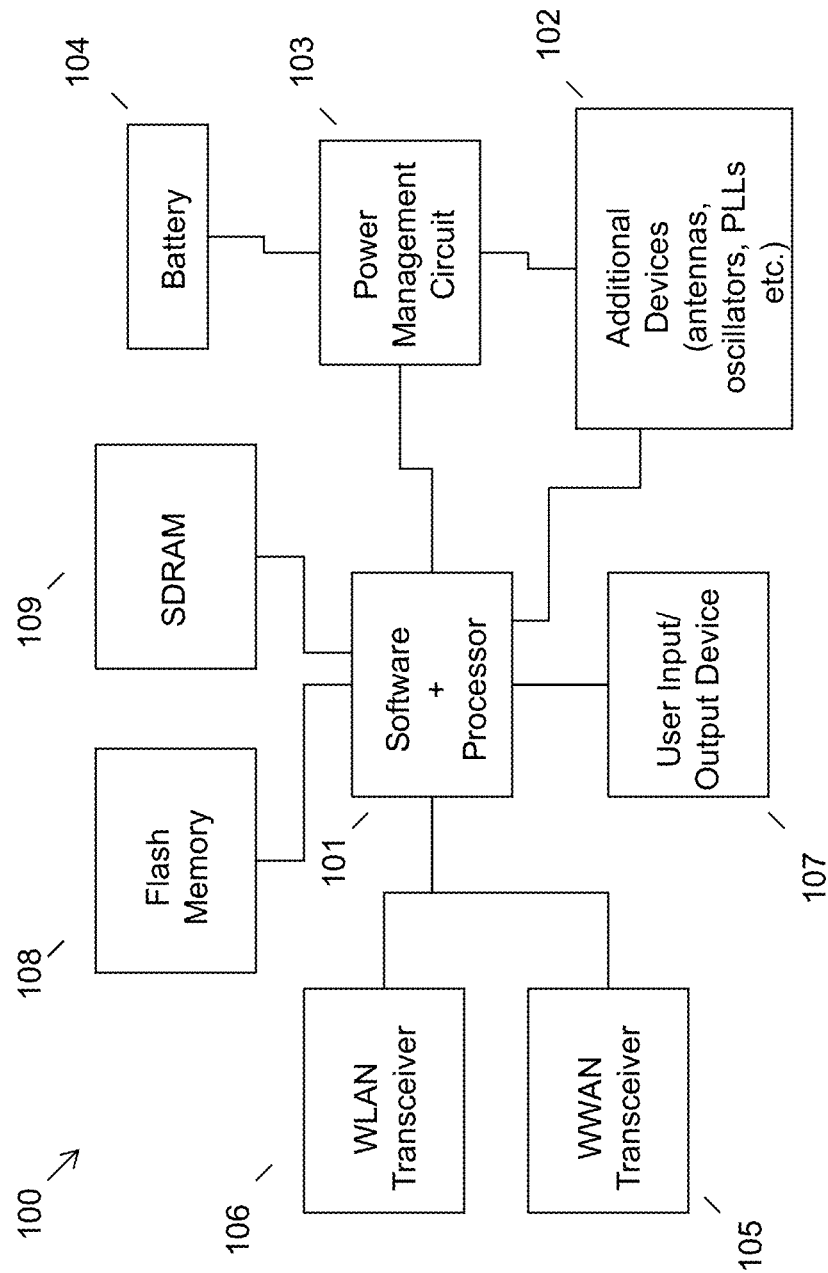
FIG. 1 illustrates an example of computer circuitry

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of the alkalinity of water or other aqueous solution or sample is very common and allows for determination of the quality of the aqueous solution. While some alkalinity measurement instruments are available, these instruments are expensive, complex, and not responsive enough for online monitoring or control. Typical water quality analysis tests for alkalinity are often performed manually using time consuming titrations. A conventional alkalinity measurement technique requires that a user manually add a strong acid to the aqueous sample to determine, by titration, the alkalinity of the sample. One technique requires a careful addition of sulfuric acid into a solution and the determination of an end-point that can be correlated to the alkalinity of the sample.

One online alkalinity measurement system performs alkalinity measurements using an electrochemical cell. Such an online alkalinity determination system may use electrochemical reactions for producing the acid (i.e., protons) in situ. These online electrochemical methods may generate protons in situ through oxidation of water within the sample itself. The generation of protons in situ from the sample eliminates the need for metering reagents such as acid delivery in a manual titration reaction. Thus, online electrochemical titration methods may be easier to use and do not require concentrated acid.

In this system, the proton generation can be correlated to the alkalinity of the water. For example, the proton generation is generally calculated based on the electron flow assuming for each electron passed, one H+ is generated. However, these systems require a "clean" sample, where no other interferants are present in the sample. In other words, the correlation of the proton generation to the alkalinity is theoretical and does not always work in practice because many samples include interferants. If water is oxidized at high current or voltages, other species, (i.e. interferences), may also be oxidized in addition to the water. For example, if the sample includes chloride, the chloride can also oxidize during electrochemical generation of protons and contribute to the total current measured; resulting in an inaccurate determination of the alkalinity of the sample (see "Automatic online buffer capacity (alkalinity) measurement of waste water using an electrochemical cell," Liang Cheng, Wipa Charles, and Ralf Cord-Ruwisch-Environmental Technology, 2016, 7 Apr. 2016). In other words, because more charge is delivered to oxidize a sample, determining an end-point from the total charge delivered from the oxidation of water and the interfering species can yield an improper and inaccurate alkalinity value. Thus, a limitation of the online electrochemical method may be the oxidation of additional interferants within the test sample.

Accordingly, the systems and methods described herein provide a technique for online alkalinity measurement that is able to determine the electrical signal attributed to the oxidation of interferants and the electrical signal that is a result of the water oxidation. Specifically, the systems and methods as described herein are able to differentiate the interferants by identifying the oxidation response that occurs below the water oxidation threshold and that which occurs at or above the water oxidation threshold. The method may use a sequence of measurements as a means to quantify the interferant species. In an embodiment, a series of voltages may be applied below the oxidation threshold of water. The current passed before reaching the oxidation of water may be measured and correlated to the interferant species in a sample. Thus, the charge that is delivered before reaching the oxidation threshold of water may be used to compensate the total charge measured to attain the titration end-point to account for interfering species in determining an alkalinity value.

In another embodiment, one or more electrical signals below the oxidation threshold of water are maintained until a certain end-point, such as current response, is attained. This embodiment provides for the elimination of the interfering species through bulk electrolysis. After this first process, a second one or more electrical signal(s) is applied at or beyond the oxidation threshold to oxidize water. This second process is used to determine the end point that enables the measurement of alkalinity.

Figure 5:
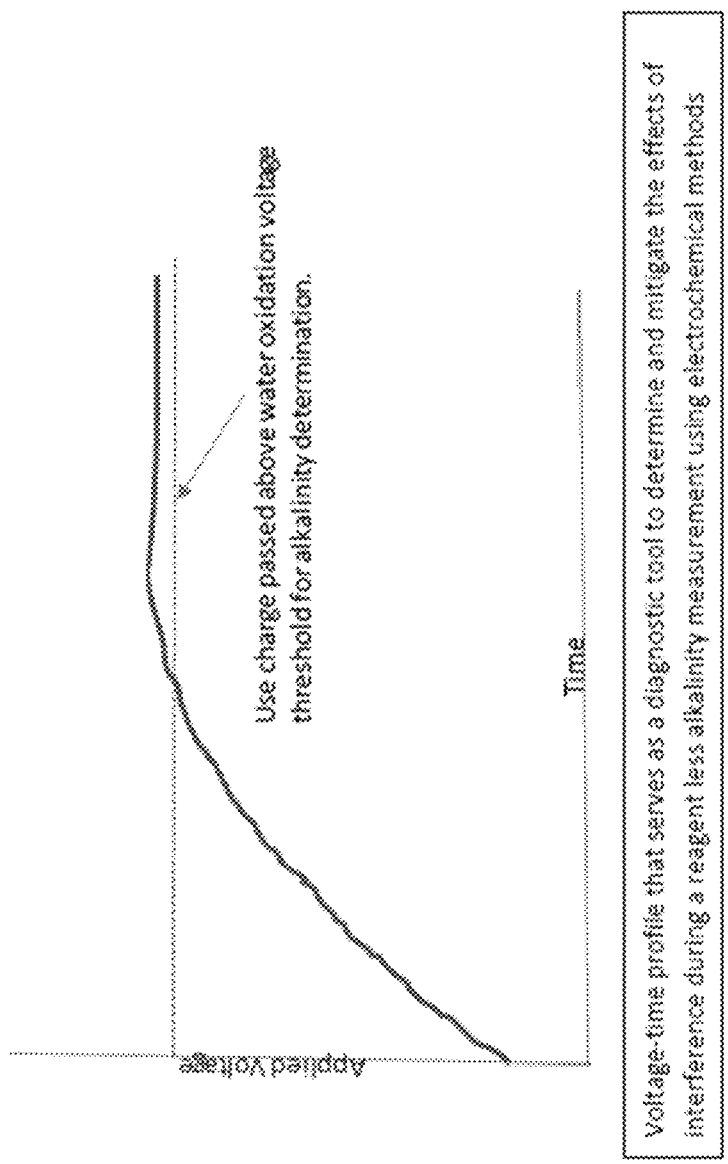
FIG. 5 illustrates an example of an oxidation threshold in an aqueous sample.

In an embodiment, an electrical signal (e.g., voltage, current, etc.) may be applied and an electrical response (e.g., voltage, current, etc.) may be monitored to quantify a charge delivered at each of a series of measurement points (e.g., water oxidation threshold, end-point, etc.). In an embodiment, the method may apply an electrical signal that will not result in the electrical signal reaching the oxidation potential of water. However, other redox species (e.g., chloride, etc.) may be oxidized at this electrical signal and an electrical response may be monitored. In other words, interferants present in the sample may be oxidized at the electrical signal values below the oxidation threshold of water. The electrical signal may then be increased to reach the solvent breakdown or water oxidation threshold. For example, FIG. 5 illustrates an electrical response to an applied voltage. The threshold line identifies the oxidation voltage threshold for oxidizing water. Any electrical response at or above this threshold can be used to determine the alkalinity of the water. Any electrical response below this threshold can be attributed to interfering species.

The system can then account for the electrical response that is attributable to the interferants and may then more accurately quantify the amount of interferants contributing to the overall charge delivered. By correcting for this electrical response attributable to the interferants, the system may determine the electrical charge that is attributable to the oxidation of the water and may then more accurately correlate this value to the alkalinity of the water or aqueous sample. In other words, if an electrical signal is applied to oxidize all the redox active species oxidized below the water oxidation threshold potential interferant species that are present (i.e., chloride, etc.) may be measured. As time progresses the applied electrical signal value increases to the oxidation threshold of water, thereafter the electrical response can be used for determination of the alkalinity of the sample. In an embodiment, the method may measure the electrical response and integrate the charge to determine an interferant species contribution. The method may therefore mathematically account for interferences by utilization of the two or more electrical responses to remove the charge delivered to interferant species that may result in false positives regarding the alkalinity values.

The illustrated example embodiments will be best understood by reference to the figures. The following description is intended only by way of example, and simply illustrates certain example embodiments.

While various other circuits, circuitry or components may be utilized in information handling devices, with regard to an instrument for alkalinity testing according to any one of the various embodiments described herein, an example is illustrated in FIG. 1. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform alkalinity tests of an aqueous sample.

Figure 2:
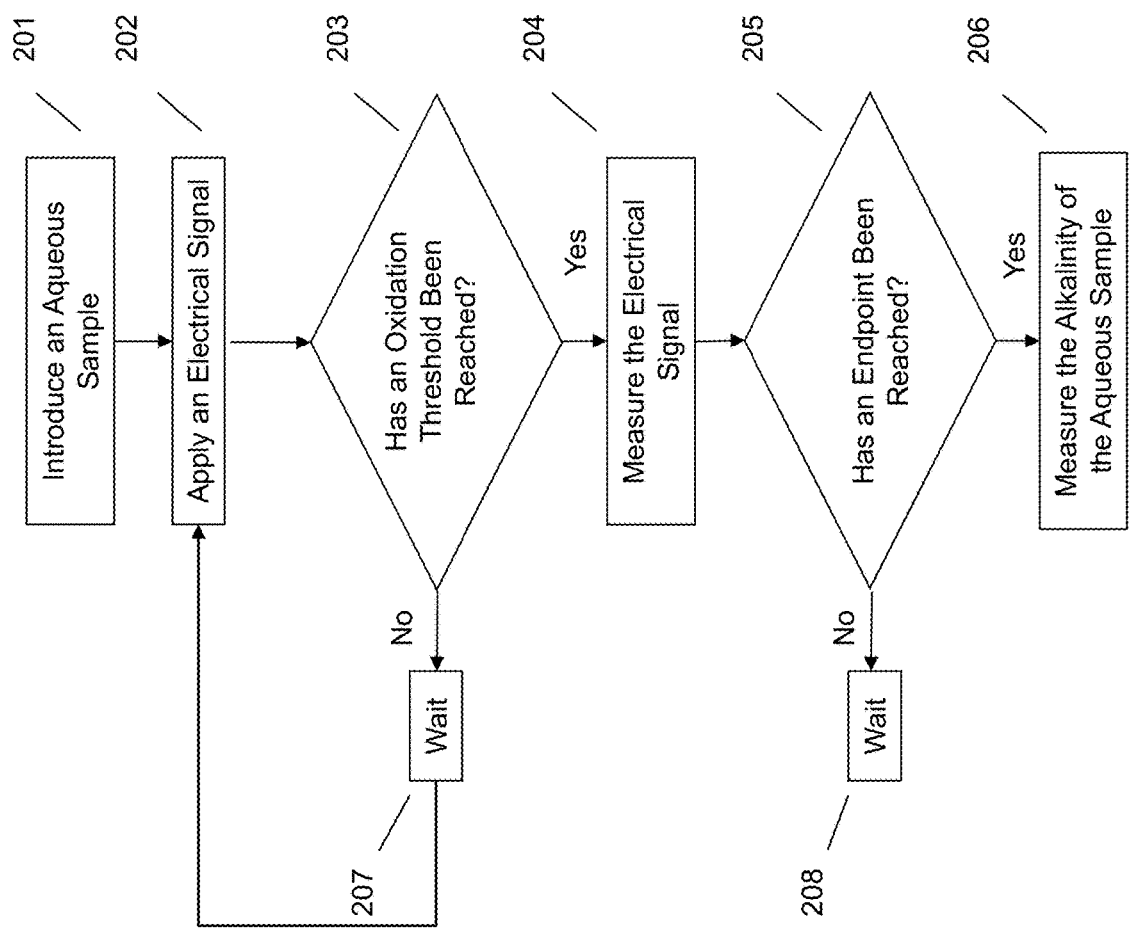
FIG. 2 illustrates a flow diagram of measuring alkalinity in an aqueous sample.

Referring now to FIG. 2, an embodiment may measure alkalinity in an aqueous solution. In an embodiment, reagents such as an acid are not required to perform an alkalinity measurement, as required in traditional methods. The systems and methods as described herein provide a technique for interference-free measurement for alkalinity values that can be used in practice with actual aqueous samples without having incorrect alkalinity value measurements. At 201, in an embodiment, an aqueous sample may be introduced into a test chamber. The aqueous sample may be placed or introduced into a test chamber manually by a user or using a mechanical means, for example, gravity flow, a pump, pressure, fluid flow, or the like. For example, a water sample for alkalinity testing may be introduced to a chamber by a pump. In an embodiment, there may be one or more chambers in which the one or more method steps may be performed. In an embodiment, valves or the like may control the influx and efflux of the aqueous solution into or out of the one or more chambers, if present. Once the sample is introduced to the measurement system, the system may measure the pH of the sample. This pH value may be used to determine whether the titration end point values have been reached. For example, the pH value that may indicate that the titration end point values may be between pH 4.3 and pH 4.5.

At 202, in an embodiment, the system may apply an electrical signal to the volume of aqueous solution in a chamber. The electrical signal may be applied using one or more electrodes, for example, a series of electrodes. Electrodes may include a working electrode, counter (auxiliary) electrode, reference electrode, or the like. In an embodiment, the one or more series of electrodes may be boron doped diamond (BDD) electrodes. The use of BDD serves as a better electrode material than other carbon-based or metallic materials (e.g., silver, gold, mercury, nickel, etc.) because these materials may eventually themselves become oxidized, thereby generating interfering signals and contributing to the errors in the measurement of alkalinity. Thin film BDD electrodes may undergo thermal stress because of the different thermal expansion coefficients between the substrate and the BDD layer, which limits the current density that can be applied to these electrodes. Thick BDD solid electrodes do not have the substrate and therefore the structural and electrical integrity may be maintained at a higher current. The lack of substrate in the thick, solid, free-standing BDD electrode eliminates the problem of delamination that can occur on thin-filmed BDD materials.

Figure 6:
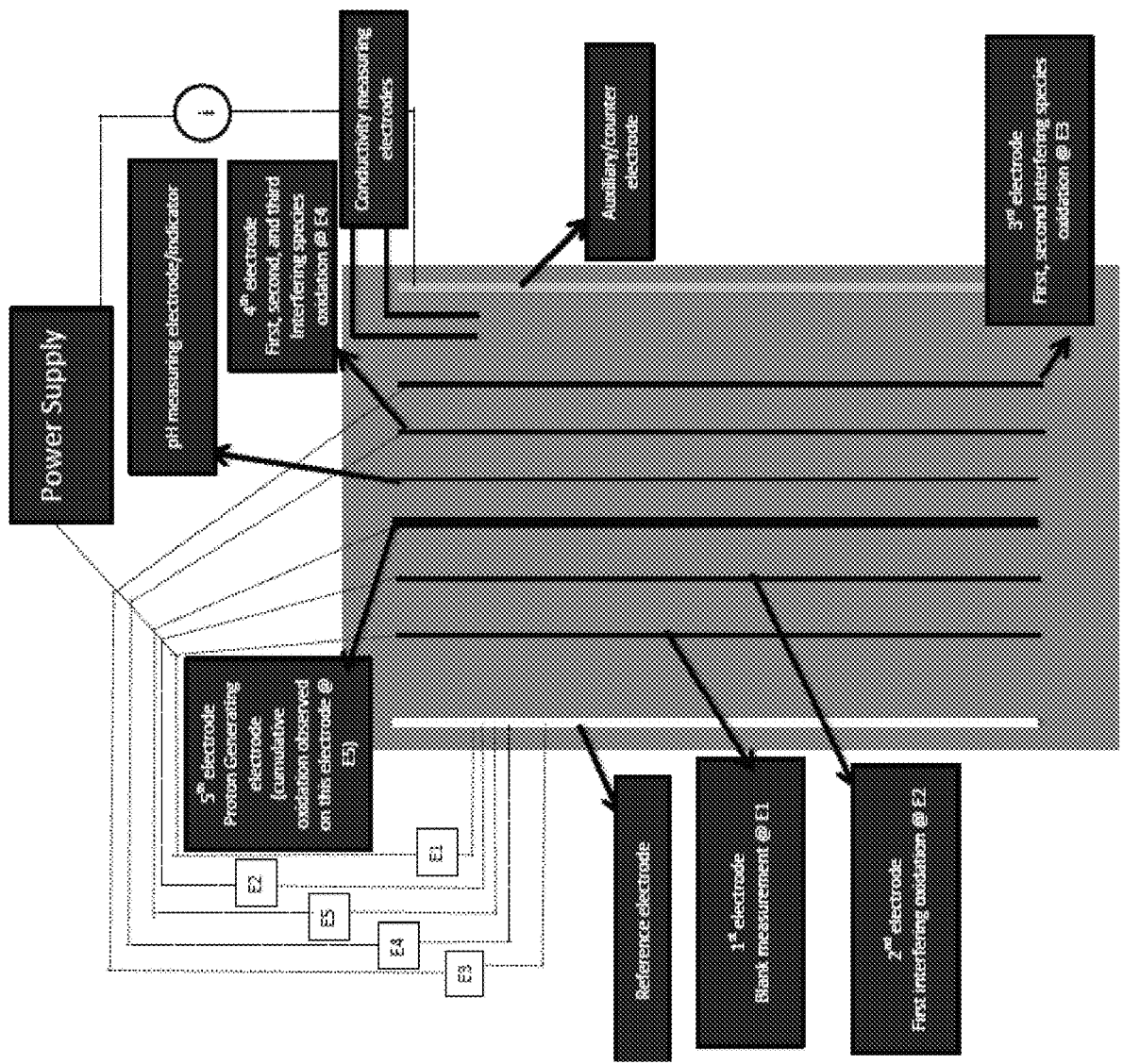
FIG. 6 illustrates an example multi-electrode system for measuring alkalinity in an aqueous sample.

The one or more electrodes may be included in one or more of the chambers of the measurement device, for example, see FIG. 6 illustrating a multi-electrode measurement device. In an embodiment, multiple electrodes may compensate for interfering redox species that may be oxidized or reduced during a production of protons for alkalinity measurement. For example, there may be a plurality of electrodes poised at different potentials. One or more electrodes may be designed to function at a high potential to generate protons and oxidizing species that are redox reactive. The use of a plurality of electrodes may allow for differentiation between different species reduced or oxidized at various potentials of an electrode. In an embodiment, at 208, if an endpoint has not been reached, the system may wait at the applied signal and/or apply subsequent electrical signal after the measurement of pH to generate a sufficient amount of protons to neutralize the buffer capacity that facilitates the determination of alkalinity.

In an embodiment, the electrodes may be fully or at least partially disposed in the volume of aqueous solution. For example, if the aqueous solution is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous solution is introduced into the chamber it only covers the portion of the electrodes that are within the chamber.

In an embodiment, the electrical signal applied at 202 may be an applied current. For example, an aqueous sample to be tested may be introduced to a chamber containing one or more series of electrodes. In an embodiment, the electrical signal applied to the electrodes, and thereby to the aqueous solution, may be a current signal. In another embodiment, the electrical signal may be a voltage. Thus, the electrical signal applied to the electrodes, and thereby to the aqueous solution, may be a voltage signal. The system may also use a combination of electrical signals, for example, by initially applying a current and then applying a voltage. The system can then measure the electrical response (e.g., current value, voltage value, etc.) that results from the application of the electrical signal to the aqueous solution.

The applied electrical signal may be any electrical signal selected from a waveform group, for example, a pulse, a step, a ramp, a sawtooth, a sine wave, a square, a triangle, a continuous signal, or the like or any combination thereof. Thus, the applied electrical signal may be applied as a constant signal or may be applied as pulses or intermittent electrical signals. In an embodiment, the amplitude may be the same or variable. For example, a first amplitude may be applied and then a second amplitude may be applied. In an embodiment, the period may be the same or variable. The electrical signal may be a preprogrammed waveform, may be altered during a measurement, and/or may be controlled by the system or by a user.

Circuitry may control the electrical signal (e.g., current, voltage, etc.) to one or more series of electrodes such that different electrical signals may be applied to the volume of aqueous solution. In the case that multiple or a series of electrodes are included in the system, each electrode may correspond to a different electrical signal value. For example, a first electrode may correspond to a first electrical signal value, a second electrode may correspond to a second electrical signal value, and the like. Each of these different electrical signal values may provide an electrical signal that will oxidize particular interferants or the aqueous solution, for example, as illustrated in FIG. 6. Thus, as the system provides electrical signals to each of the electrodes in series, different components of the aqueous sample may be oxidized. In the case that a single electrode is used, the system may apply different electrical signals to the single electrode, each with an increasing electrical signal value. In either case, after each application of an electrical signal, the system may measure the pH of the aqueous solution to determine whether the pH indicates that the titration end point has been reached. It should be understood that when discussing the series of electrodes or the single electrode, this refers to the electrodes that generate the protons within the system. Thus, other electrodes may be included to complete the electrical circuit or to provide a reference electrode for measurement, for example, even in the case of a single electrode the system may include a reference electrode, an auxiliary electrode, or the like.

Figure 4:
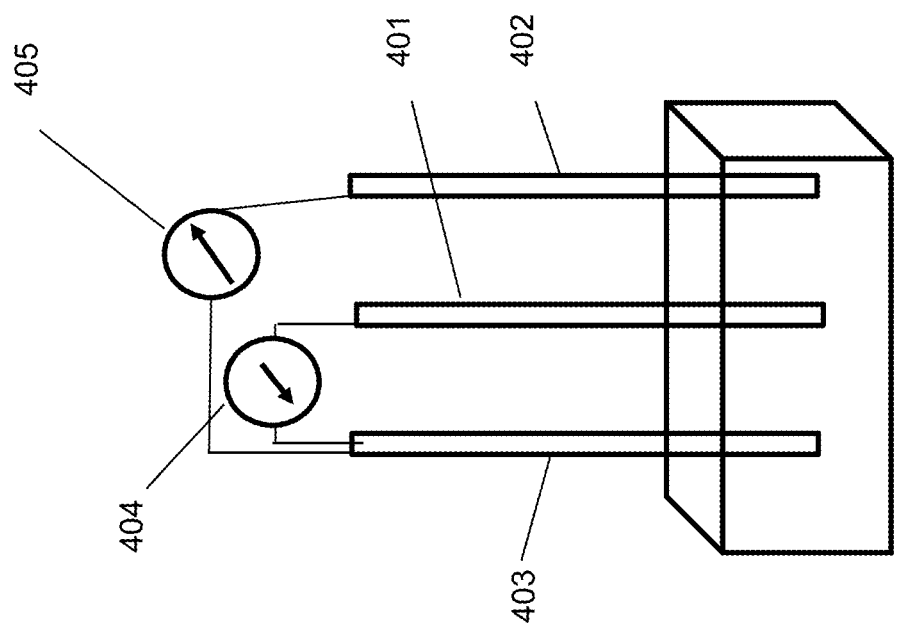
FIG. 4 illustrates an example device for measuring alkalinity.

A simplified version of the measurement system is illustrated in FIG. 4 with a three-electrode system. The electrodes may include a counter electrode 401, a working electrode 403, a reference electrode 402, and/or the like. A counter electrode 401 (sometimes referred to as an auxiliary electrode) may be used to close the circuit in an electrochemical cell and may be used to close the circuit with a reference electrode and a working electrode. A reference electrode 402 may be maintained at a near zero or zero current flow using impedance. A working electrode 403 may be an electrode in which the electrochemical reaction of interest is occurring. In this example system, an electrical signal 404 may be applied to the aqueous solution between two electrodes. In the case of the application of current; as the signal is applied between working and counter, the voltage response is measured between the working and the reference or electrical ground. In the case of the application of voltage; as the signal is applied between the reference 401 and working electrodes the current response is measured between the working and the counter electrodes.

At 203, an electrical signal may be applied until an oxidation threshold, for example, as illustrated in FIG. 5, has been reached. An application of an electrical signal to the aqueous sample across the one or more series of electrodes may oxidize species contained in the aqueous sample. Different species contained in the aqueous sample may oxidize at different potentials depending on a particular species contained in the aqueous sample. Through application of an electrical signal and resulting measurements, the chemical composition of the aqueous sample may be determined.

For example, an aqueous sample may contain one of more species in the water. An electrical signal-time profile may serve as a diagnostic tool to determine and mitigate effects or interferant species during an alkalinity measurement using described electrochemical methods. As the applied electrical signal increases, species in the aqueous sample may become oxidized at different applied electrical signal values. Thus, interferants may be oxidized at an applied electrical signal value lower than the water oxidation threshold. In one embodiment to determine if the oxidation threshold has been reached, the system may measure the pH of the aqueous solution after application of one or more of the electrical signals. Different pH values may indicate the chemical composition of the aqueous solution. For example, it may indicate that all oxidation is solely due to interferants if the pH value does not decrease between electrical signal applications and measurements. The use of a plurality of electrodes may allow for a more precise measurement. For example, if there is an overlap between production of protons and a next hardest oxidizable species, then an intermediate potential electrode may be able to deconvolute an overlapping signal between the generation of protons and the next hardest oxidizable species. At 207, if an oxidation threshold is not reached, the system may wait and continue applying an electrical signal at 202 to reach the oxidation threshold.

If, however, the water oxidation threshold has been reached at 203, the system may, at 204, measure an electrical response within the aqueous solution to the electrical signal. Specifically, the system may take a measurement of the charge that has been thus far applied to the aqueous solution. This charge may then be attributed to the interferants that were in the aqueous solution. In other words, once the system identifies that the oxidation threshold has been met, the system may determine that any charge that is measured after the threshold is attributable to the alkalinity of the aqueous solution. Thus, to determine the alkalinity the system identifies the charge value that is attributable to the interferants. In other words, the system effectively "zeros" the charge contribution to the alkalinity measurement at the point that the oxidation threshold has been met.

While applying the electrical signal and measuring the response, the system, at 205, may determine if an endpoint of the electrochemical reaction has been reached. This determination may be made based upon the pH value of the aqueous sample. In other words, after application of the electrical signal, the system may measure the pH value of the aqueous sample. Once the sample reaches a particular pH value, the system may identify this value as the endpoint. For example, a pH value between 4.3 and 4.5 may indicate that the endpoint for determining the total alkalinity has been reached. If the endpoint has not been reached at 205, the system may continue to apply an electrical signal and measure the response of the system at 208 until the endpoint is reached.

If, however, the endpoint has been reached at 205, the system, at 206, may measure an alkalinity of the aqueous sample. The alkalinity measurement may be based upon a comparison of the first electrical response with the aqueous solution to an electrical signal, for example, the electrical response that was measured at the point of the oxidation threshold to the second electrical response, for example, the electrical response that was measured at the endpoint. In other words, the system subtracts the charge measurement associated with the oxidation threshold from the charge measurement associated with this endpoint. The system can then correlate this value to an alkalinity measurement. Using this differentiation method, the system may obtain a clean quantitative signal for the proton generation which may be used to determine a buffer capacity and alkalinity of the aqueous sample. In an embodiment, a comparison of measurement from one or more series of electrodes may be performed over time.

In an embodiment, an alkalinity of a sample may be based upon a number of protons generated in an aqueous sample. In an embodiment, the measuring may use a correlation between the different (as calculated above) and a pH of an aqueous sample. Alkalinity may be quantified using many methods such as M-alkalinity (a.k.a T-Alkalinity), P-Alkalinity, or the like. M-alkalinity may be a measure of the amount of acid or protons requires to drop a pH to a value of about 4.3. P-alkalinity may be a measure of the amount of acid or protons requires to drop a pH to a value of about 8.3. Instead of using harsh acid reagents that may need to be added or titrated by a user, an embodiment generates proton through an electrochemical process, for example, by applying an electrical signal to the aqueous solution. In an embodiment, the presence of other redox species in an aqueous sample may be subtracted. For example, if chlorine is present an applied potential will oxidize the chloride in the aqueous sample. Thus, the system may subtract other species that contribute to oxidation current that may result in an inaccurate or false positive determination of alkalinity, thereby determining a more accurate measurement of the alkalinity of the aqueous solution. Accordingly, the systems and methods as described herein provide a technique for the electrochemical generation of protons that serve as a source for protons instead of the addition or titration of an acid (e.g., sulphuric acid) as required in traditional techniques.

Figure 3:
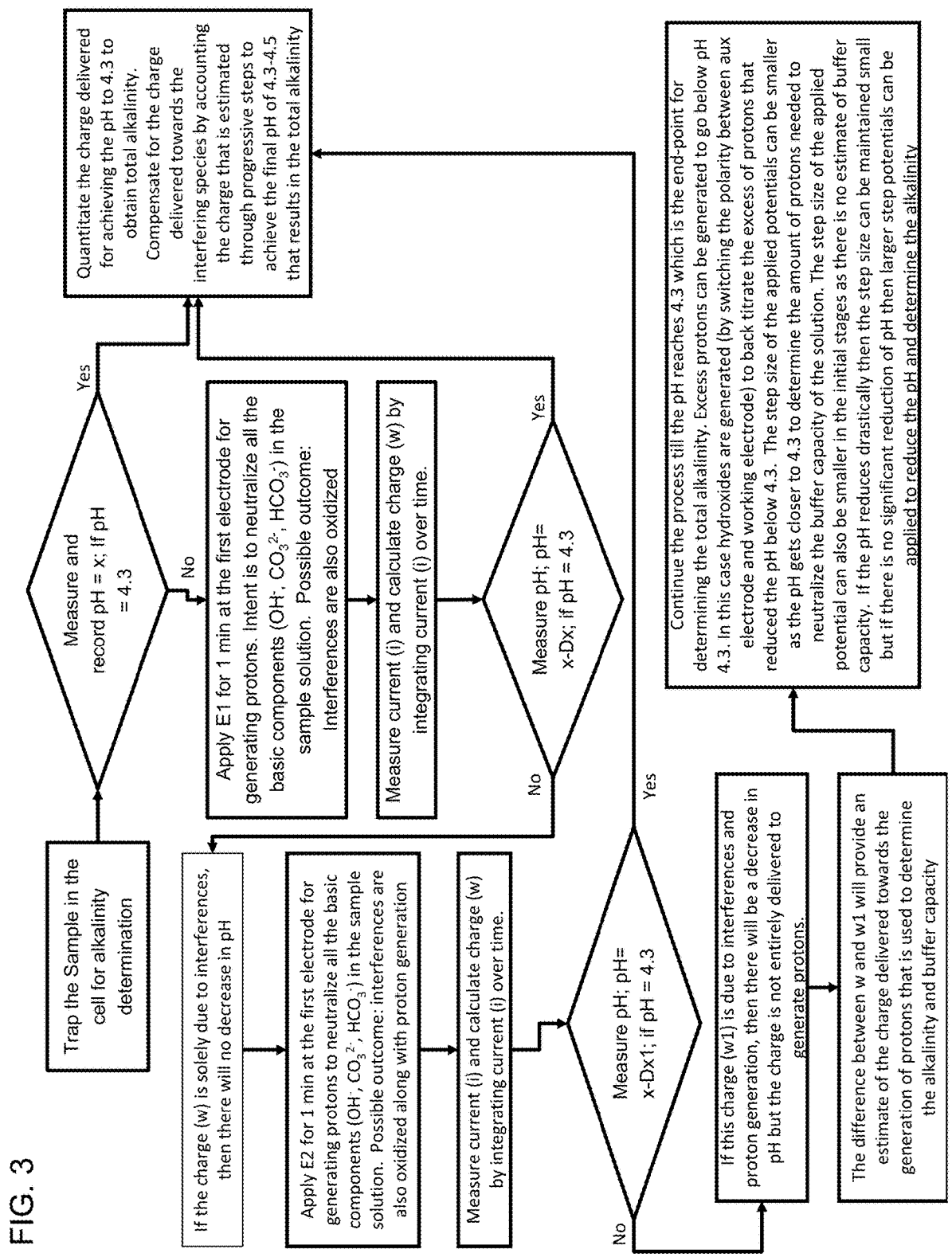
FIG. 3 illustrates a flow diagram of measuring alkalinity in an aqueous sample in an example embodiment.

Referring to FIG. 3, an example embodiment of a method for measuring alkalinity of an aqueous sample is illustrated. In an embodiment, the system traps the sample in the cell for alkalinity determination, and measures and records the pH. If the pH is 4.3, then the system quantitates the charge delivered for achieving the pH to 4.3 to obtain total alkalinity. An embodiment may also compensate for the charge delivered towards the interfering species by accounting the charge that is estimated through progressive steps to achieve the final pH of 4.3-4.5 that results in the total alkalinity. If the pH has not reached 4.3, apply E1 for 1 min at the first electrode for generating protons. In an embodiment, an intent is to neutralize all the basic components ($OH^-$, $CO_3^{2-}$, $HCO_3^-$) in the sample solution which may oxidize interferences, and measure current (i) and calculate charge (w) by integrating current (i) over time. If the charge is solely due to interferences, there may be no decrease in pH, thus apply E2 for 1 min at the first electrode for generating protons to neutralize all the basic components ($OH^-$, $CO_3^{2-}$, $HCO_3^-$) in the sample solution (Possible outcome: interferences are also oxidized along with proton generation), and measure current (i1) and calculate charge (w1) by integrating current (i1) over time. In an embodiment, the system may check to see if the pH has reached 4.3 (pH=x−Dx1), and if this charge (w1) is due to interferences and proton generation, then there will be a decrease in pH but the charge is not entirely attributed to generate protons. The difference between w and w1 will provide an estimate of the charge delivered towards the generation of protons that is used to determine the alkalinity and buffer capacity. In an embodiment, the process may continue until the pH reaches 4.3 which is the end-point for determining the total alkalinity. Excess protons can be generated to go below pH 4.3. In this case hydroxides may be generated (by switching the polarity between aux electrode and working electrode) to back titrate the excess of protons that reduced the pH below 4.3. The step size of the applied potentials can be smaller as the pH gets closer to 4.3 to determine the amount of protons needed to neutralize the buffer capacity of the solution. The step size of the applied potential can also be smaller in the initial stages as there may be no estimate of buffer capacity. If the pH reduces drastically then the step size can be maintained small but if there is no significant reduction of pH then larger step potentials can be applied to reduce the pH and determine the alkalinity.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for compensating for interferants in measurement of alkalinity in a reagent-less system, comprising:
    introducing an aqueous sample into a measurement device comprising one or more series of electrodes, wherein the one or more series of electrodes comprises a working electrode;
    applying an electrical signal to the aqueous sample using the one or more series of electrodes, wherein the electrical signal is selected from the group consisting of: current and voltage;
    identifying, during application of the electrical signal via the working electrode, that the electrical signal reaches an oxidation threshold of water and measuring, at the oxidation threshold, a first electrical response to the electrical signal measured by at least the working electrode, the first electrical response attributable to interferants in the aqueous sample;
    identifying, during application of the electrical signal via the same working electrode, that the electrical signal reaches an endpoint of an electrochemical reaction at a predetermined pH and measuring, at the endpoint, a second electrical response to the electrical signal measured by at least the same working electrode; and
    measuring an alkalinity of the aqueous sample based upon a difference between the first electrical response and the second electrical response.

2. The method of claim 1, wherein the measurement device comprises more than one chamber.

3. The method of claim 1, wherein the electrical signal is voltage; and further comprising converting the measured first electrical response to a corresponding current.

4. The methods of claim 1, wherein the electrical signal is current, and further comprises converting the measured first electrical response to a corresponding charge.

5. The method of claim 1, wherein the one or more series of electrodes comprise at least one electrode selected from the group consisting of a working electrode, a counter electrode, and a reference electrode.

6. The method of claim 1, wherein the one or more series of electrodes comprises electrodes selected from the group consisting of: boron doped diamond based electrodes and a combination of sp3/sp2 boron doped diamond electrodes.

7. The method of claim 1, wherein the applying comprises applying an electrical signal selected from the waveform group consisting of a pulse, a step, a ramp, and a continuous electrical waveform.

8. The method of claim 1, wherein the alkalinity is based upon a number of protons generated in the aqueous sample from application of the electrical signal.

9. The method of claim 1, wherein the alkalinity is based upon the determination of the charge delivered to obtain the protons generated during the process using electrochemical equations.

10. The method of claim 1, wherein the measuring comprises a correlation between the difference between the first electrical response and the second electrical response and a pH of the aqueous sample.

* * * * *